United States Patent [19]

Nano et al.

[11] Patent Number: 5,075,228

[45] Date of Patent: Dec. 24, 1991

[54] **RECOMBINANT CLONES OF *CHLAMYDIA TRACHOMATIS* LIPOPOLYSACCHARIDE**

[75] Inventors: Francis E. Nano; Harlan D. Caldwell, both of Hamilton, Mont.

[73] Assignee: United States of America, Washington, D.C.

[21] Appl. No.: 590,443

[22] Filed: Sep. 27, 1990

Related U.S. Application Data

[63] Continuation of Ser. No. 433,424, Nov. 8, 1989, abandoned, which is a continuation of Ser. No. 707,012, Feb. 28, 1985, abandoned.

[51] Int. Cl.[5] ...................... C12N 15/00; C12N 15/72

[52] U.S. Cl. .................................... 435/172.3; 435/6; 435/7.1; 435/7.37; 435/69.3; 435/252.33; 435/320.1

[58] Field of Search ..................... 435/6, 7, 69.3, 71.2, 435/91, 172.1, 172.3, 193, 200, 252.3, 252.31-252.35, 320, 320.1; 436/510; 536/27; 935/14, 23, 50, 73

[56] References Cited

PUBLICATIONS

Wenman et al., "Expression in *E. coli* of *Chlamydia trachomatis* Antigen Recognized During Human Infection", Nature 296: 68 (1982).

Allan et al., "Molecular Cloning of the Major Outer Membrane Protein of *Chlamydia trachomatis*", Infec. Immun. 45: 637 (1984).

Curtiss, "Antigenic Products of Recombinant Genes and Related Vaccines", Chem; Abstr. 99: 146100y (1983) of Eur. Pat. Appl. EP 80, 806 (Jun. 8, 1983).

*Primary Examiner*—James Martinell

*Attorney, Agent, or Firm*—Cushman, Darby & Cushman

[57] ABSTRACT

Disclosed is a clone and the process for cloning genes encoding the genus-specific lipopolysaccharide antigen of chlamydia. The clone is a hybrid lipopolysaccharide molecule composed of both chlamydia and *E. coli* components.

10 Claims, No Drawings

RECOMBINANT CLONES OF *CHLAMYDIA TRACHOMATIS* LIPOPOLYSACCHARIDE

This application is a continuation of application Ser. No. 07/433,424 Nov. 8, 1983 which is a continuation of application Ser. No. 06/707,012, filed Feb. 28, 1985, now abandoned.

BACKGROUND

Chlamydia are obligate intracellular procaryotes that are structurally similar to gram-negative bacteria. There are two species, *Chlamydia trachomatis* and *C. psittaci. C. trachomatis* is a specific human pathogen, whereas *C. psittaci* is a pathogen of a variety of non-primate species. Diseases caused by *C. trachomatis* present a major health problem throughout the world. In developing countries, *C. trachomatis* causes hyperendemic trachoma which is the world's leading cause of preventable blindness. There are approximately two million people in the world today who are blind as a result of trachoma and an estimated 500 million more who are affected by this disease. In industralized nations, *C. trachomatis* is a sexually transmitted pathogen that causes an array of genital tract and associated infections whose incidence is increasing at epidemic rates. Conservative estimates indicate that in the United States alone there are 7–10 million *C. trachomatis* infections per year. In addition to their vertebrate hosts, chlamydial-like organisms have also been identified in tissues of spiders (*Coelotus luctuosus*) and clams (*Mercenarie mercenaria*), suggesting that chlamydiae are ubiquitous parasites present throughout the animal kingdom.

Biologically, Chlamydia are distinguished from all other intracellular procaryotes by their unique life cycle and molecular mechanisms of pathogenesis. The life cycle consists of two cell types, the elementary body and the reticulate body, which differ both morphologically and functionally. The elementary body is the extracellular cell type; it is metabolically inactive and is the infectious form of the parasite. The elementary body is unique in that it is efficiently phagocytized, even by nonprofessional phagocytes, and once internalized, it prevents phagolysosomal fusion. Mediators of these pathogenic mechanisms are believed to be surface components of the elementary body; however, their identity and biochemical nature is currently unknown.

Despite their common biology, *C. trachomatis* and *C. psittaci* share only 10% DNA homology and demonstrate little antigenic relatedness among their surface protein constituents. They do, however, share a common outer membrane qlycolipid antigen that has been shown to be a lipopolysaccharide (LPS) antigenically similar to the Re LPS chemotype isolated from mutants of Salmonella spp. (Caldwell et al: Inf. & Imm. 44 : 306–314 [1984]). Despite the similarities between chlamydial LPS and the Re LPS of enteric bacteria, chlamydial LPS contains a periodate sensitive antigenic determinant that is common to Chlamydia but is not found in a variety of enteric bacteria. This antigenic determinant has been defined by monoclonal antibody and termed the genus-specific LPS antigen (see Caldwell et al, above). The biological function of chlamydial LPS is unknown, but the conserved nature of the LSP epitope in an otherwise antigenically diverse genus suggests that this epitope may be functionally important with respect to the molecular mechanisms of pathogenesis shared by these obligate intracellular parasites.

The clone JM109(pFEN207), equivalent to ATCC Accession No. 53041, was deposited in the American Type Culture Collection on Feb. 27, 1985, in the patent deposit for a term of at least thirty years and complying with the time requirements of the Budapest Convention.

Utility

The recombinant clones of the present invention are used for the development of simple, rapid, and inexpensive serologic or antigen assays for diagnosing and treating infections caused by *Chlamydia trachomatis* or *C. psittaci.*

SUMMARY OF THE INVENTION

The clones of the present invention are produced from chlamydia a gene bank selected from, a *C. trachomatis* was partially digested with Sau3A. DNA of 4–6 kilobases is pooled and then cloned into BamHI digested alkaline phosphatased *E. coli* pUC8. These clones possess an antigen reactive with monoclonal antibodies directed against the genus-specific LPS epitope.

SPECIFIC DISCLOSURE

Whole genomic DNA from *C. trachomatis* is isolated and digested partially with Sau3A restriction enzyme. Partially digested DNA is then sized by agarose gel electrophoresis; DNA of 4–6 Kb is isolated, pooled, and ligated into a suitable *Bam*HI digested plasmid. The ligated plasmid mixture is then transformed into *E. coli*, and ampicillin resistance *E. coli* were selected (indicating recombinants containing *C. trachomatis* DNA). They are then screened for the presence of chlamydial specific antigens using polyclonal antibody directed against *C. trachomatis* elementary bodies. Several *E. coli* recombinants reacted with the antibodies: these are then screened with monoclonal antibodies directed against different antigens. Several of the recombinants reacted with lipopolysaccharide epitope of *C. trachomatis* (also found of *C. psittaci*) and these recombinants were further characterized by examining the DNA with restriction endonucleases in vitro transcription translation of the isolated plasmid and other biochemical techniques.

A preferred plasmid for use in this process is pUC8, commercially available from Pharmacia. pUC8 and other suitable plasmids, contain a relatively strong promoter region which aids in expression of the chlamydial genes. Specifically, this promoter is the lac operon promoter.

A preferred strain of *E. coli* is strain JM109, also commercially available. This particular strain is compatible with pUC8 due to a lesion of the lac operon on the chromosome.

Although a preferred plasmid and bacterial strain are disclosed, other plasmids and *E. coli* strains may be used provided that the plasmid contains a *lac* promoter and the *E.* coli strain complements the plasmid.

EXAMPLE 1

An experiment was conducted to determine whether the chlamydial LPS epitope was exposed on the surface of the *E. coli* recombinant. Fluorescent antibody staining of heat-fixed pFEN207 cells with the chlamydial LPS monoclonal antibody showed that the antigen was located at the periphery of individual cells.

Surface immunofluorescence was also observed. Surface exposure of the chlamydial LPS epitope was shown on viable *E. coli* recombinants by immunoelectron microscopy. When viable pFEN207 cells were reacted with monoclonal antibody and protein A colloidal cold and then examined by electron microscopy without subsequent fixation or staining, electron dense gold particles were specifically bound to the surfaces of the recombinant clone expressing the chlamydial LPS epitope.

EXAMPLE 2

From a gene bank of *C. trachomatis* (strain LGV-434) DNA, we identified several recombinants that were immunoreactive with rabbit polyclonal antibody raised against viable LGV-434 elementary bodies. Four of these non-sibling recombinants were subsequently shown by immunoblots of polyacrylamide gels to possess an antigen reactive with monoclonal antibody directed against the genus-specific LPS epitope. One of these *Escherichia coli* recombinants, JM109 (pFEN207), was studied in more detail. Analysis of whole-cell preparations and phenol-water extracts of chlamydial elementary bodies and *E. coli* recombinants by polyacrylamide gel electrophoresis showed that the JM109 (pFEN207) recombinant possessed three distinct species of LPS. Two of the LPS species were found in the parent *E. coli* strain harboring the pUC8 plasmid. A third LPS species was unique to the recombinant strain and reacted with monoclonal antibody against the chlamydial genus-specific LPS epitope by immunoblotting analysis. The immunoreactive LPS found in the recombinant clone pFEN207 migrated with an increased electrophoretic mobility relative to native chlamydial LPS. This molecule is a hybrid LPS composed of both an *E. coli* and chlamydial LPS component. The pFEN207 plasmid contains a gene(s) that encodes a glycosyl transferase involved in chlamydial LPS synthesis and that the chlamydial glycosyl transferase has incorporated the carbohydrate moiety that confers the genus-specific antigenic property to chlamydial LPS on *E. coli* LPS.

We claim:

1. A method of producing clones expressing Chlamydia lipopolysaccharide epitopes comprising the steps of:
   1) partially digesting whole genomic KNA from Chlamydia with a restriction enzyme;
   2) sizing the DNA;
   3) pooling DNA of 4–6 kb;
   4) ligating DNA from (3) to a Bam Hi digested plasmid containing a lac promotor;
   5) transforming the plasmid of (4) into *E.coli*;
   6) screening *E.coli* of (5) for presence of Chlamydia-specific antigens; and
   7) selecting and maintaining *E. coli* showing presence of Chlamydia specific lipopolysaccharide antigens.

2. A process of claim 1 wherein the enzyme used in step (1) is Sau 3A.

3. A process of claim 1 wherein sizing used in step (2) is accomplished by use of agarose gel.

4. A process of claim 1 wherein sizing is accomplished using electrophoresis.

5. A process of claim 1 wherein *E. coli* used in step (5() is an ampicillin-resistant strain.

6. A process of claim 1 wherein the screening is carried out using polyclonal antibodies which specifically bind to chlamydia lipopolysaccharide antigens.

7. A method of claim 1 wherein screening and selection is accomplished using fluorescent antibody straining techniques.

8. A method of claim 1 wherein screening and selection are accomplished by use of immunoelectron microscopy.

9. A process of claim 1 wherein Protein A colloidal gold is added with the antibody to facilitate detection of Chlamydia-specific antigen in the selection process.

10. A recombinant clone depositied in the American Type Culture Collection under the accession number 53041 designated #JM109 (pFEN207).

* * * * *

UNITED STATES PATENT AND TRADEMARK OFFICE
CERTIFICATE OF CORRECTION

PATENT NO. : 5,075,228　　　　　　　　　　Page 1 of 3
DATED : December 24, 1991
INVENTOR(S) :　　FRANCIS E. NANO and HARLAN D. CALDWELL It is certified that error appears in the above-identified patent and that said Letters Patent is hereby corrected as shown below:

Col. 1, line 11, delete "Chlamydia" and insert --Chlamydia--;

line 34, delete "Chlamydia" and insert --Chlamydia--;

line 52, delete "qlycolipid" and insert --glycolipid";

line 55, delete "Salmonella" and insert --Salmonella--; and line 59, delete "Chlamydia" and insert --Chlamydia--.

Col. 2, delete lines 15-17 and insert --The clones of the present invention are selected from a chlamydial gene bank produced from C. trachomatis DNA that was partially digested with Sau3A.--;

line 26, delete "Sau3A" and insert --Sau3A--;

line 29, delete "BamHI" and insert --BamH I--;

UNITED STATES PATENT AND TRADEMARK OFFICE
CERTIFICATE OF CORRECTION

PATENT NO. : 5,075,228            Page 2 of 3
DATED : December 24, 1991
INVENTOR(S) : FRANCIS E. NANO and HARLAN D. CALDWELL It is certified that error appears in the above-identified patent and that said Letters Patent is hereby corrected as shown below:

line 42, after "endonucleases" insert --,--;

line 43, after "plasmid" insert --,--;

line 48, delete "lac" and insert --*lac*--;

line 52, delete "lac" and insert --*lac*--; and line 57, delete "coli" and insert --*coli*--.

IN THE CLAIMS:
Column 4,
Claim 1, lines 4-5, delete "Chlamydia" and insert --*Chlamydia*--;

line 6, delete "KNA" and insert --DNA--;

line 7, "Chlamydia" and insert --*Chlamydia*--; and line 16, delete "Chlamydia specific" and insert --*Chlamydia*-specific--.

UNITED STATES PATENT AND TRADEMARK OFFICE
CERTIFICATE OF CORRECTION

PATENT NO. : 5,075,228
DATED : December 24, 1991
INVENTOR(S) : FRANCIS E. NANO and HARLAN D. CALDWELL It is certified that error appears in the above-identified patent and that said Letters Patent is hereby corrected as shown below:

IN THE CLAIMS:

Column 4,

Claim 2, line 18, delete "Sau 3A" and insert --Sau3A--.

Claim 5, line 24, delete "(5()" and insert --5)--.

Claim 6, line 27, delete "chlamydia" and insert --Chlamydia--.

Claim 9, line 36, delete "Chlamydia-specific" and insert --Chlamydia-specific--.

Claim 10, line 37, delete "depositied" and insert --deposited--.

Signed and Sealed this

Eighteenth Day of January, 1994

Attest:

BRUCE LEHMAN

Attesting Officer     Commissioner of Patents and Trademarks